(12) United States Patent
Brookins

(10) Patent No.: US 10,028,497 B1
(45) Date of Patent: Jul. 24, 2018

(54) MISTING SYSTEM

(71) Applicant: ZAP MOSQUITO SOLUTIONS INC., Miami, FL (US)

(72) Inventor: Keith Donald Brookins, Miami, FL (US)

(73) Assignee: ZAP MOSQUITO SOLUTIONS INC., Miami, FL (US)

( * ) Notice: Subject to any disclaimer, the term of this patent is extended or adjusted under 35 U.S.C. 154(b) by 0 days.

(21) Appl. No.: 15/481,952

(22) Filed: Apr. 7, 2017

(51) Int. Cl.
  *A01M 1/20* (2006.01)
  *A01M 7/00* (2006.01)
  *A61L 9/12* (2006.01)

(52) U.S. Cl.
  CPC ............ *A01M 7/0017* (2013.01); *A01M 1/20* (2013.01); *A01M 1/2033* (2013.01); *A01M 1/2038* (2013.01); *A61L 9/122* (2013.01); *A61L 9/125* (2013.01)

(58) Field of Classification Search
  CPC .............. A01M 1/2033; A01M 1/2038; A01M 7/0017; A01M 7/0021; A01M 13/00; A01M 1/20; A61L 9/122; A61L 9/145; A61L 9/125
  See application file for complete search history.

(56) References Cited

U.S. PATENT DOCUMENTS

| | | | |
|---|---|---|---|
| 3,793,763 A * | 2/1974 | Griffin | A01M 1/06 43/129 |
| 7,090,147 B2 | 8/2006 | Lovett | |
| 7,320,439 B2 | 1/2008 | Davis et al. | |
| 7,540,433 B2 | 6/2009 | Fleming et al. | |
| 8,282,883 B2 * | 10/2012 | Yamasaki | A01M 1/2033 422/123 |
| 8,430,337 B2 | 4/2013 | Pearce, III et al. | |
| 8,994,529 B2 | 3/2015 | White | |
| 9,358,569 B2 | 6/2016 | Burt et al. | |
| 9,414,580 B2 | 8/2016 | Franks et al. | |
| 2006/0006197 A1 * | 1/2006 | Davis | A01M 1/2038 222/372 |
| 2008/0029614 A1 | 2/2008 | Dore | |
| 2008/0067263 A1 | 3/2008 | Modlin et al. | |
| 2009/0183689 A1 | 7/2009 | Moore et al. | |
| 2009/0265977 A1 | 10/2009 | Sullivan et al. | |
| 2010/0243754 A1 * | 9/2010 | Harris | A01M 1/2033 239/34 |
| 2014/0097273 A1 * | 4/2014 | Helms | B05B 12/02 239/337 |

* cited by examiner

*Primary Examiner* — Alexander Valvis
(74) *Attorney, Agent, or Firm* — Albert Bordas, P.A.

(57) ABSTRACT

A misting system having an external compartment, an interior housing, a container housing, an electrical compartment, a lid assembly, and at least one outlet. The external compartment has a top face with a hole, a cavity, and an electrical cover panel. The interior housing has a top face with a hole, and lateral faces with a respective pivot hole. The container housing has lateral faces having pivoting protrusions, which are positioned onto each pivot hole of the interior housing lateral faces. The electrical compartment has a cover panel, a battery and a pump assembly. The lid assembly has a locking tab, a panel locking tab, a latching-limiter rod, and a spear. The electrical cover panel of the external compartment mounts onto the electrical compartment, and the cover panel of the electrical compartment mounts onto the external compartment. The lid assembly covers the external compartment and the electrical compartment.

15 Claims, 9 Drawing Sheets

MISTING SYSTEM

BACKGROUND OF THE INVENTION

1. Field of the Invention

The present invention relates to misting systems, and more particularly, to misting systems for insect control.

2. Description of the Related Art

Applicant believes that one of the closest references corresponds to U.S. Patent Application Publication No. 20090265977 A1, published on Oct. 29, 2009 to Helen Joyce Sullivan, et al. for Portable Insect Misting System. However, it differs from the present invention because Sullivan, et al. teaches a portable, light-activated, mist sprayer system comprising direct current power supply, a container of treating fluid at a desired concentration; a motor and pump that are activated at the appropriate time as determined by the switch or timer; at least one sprayer nozzle that will dispense a mist containing the treating fluid whenever the pump is operating; and a timer that turns off the pump after a preset interval to terminate the spraying cycle. A utility for the system is spraying dilute solutions of insecticide or insect repellent in a mobile fashion while in areas away from a power source or away from larger stored amounts of insecticides.

Applicant believes that another reference corresponds to U.S. Patent Application Publication No. 20090183689 A1, published on Jul. 23, 2009 to Gary Stephen Moore, et al. for Portable, Rechargeable Insect Control Apparatus and Method of Operation. However, it differs from the present invention because Moore, et al. teaches a system for controlling insects that includes an insect control compound reservoir. A pump receives an insect control compound from the insect compound reservoir and pressurizes the insect control compound. A rechargeable battery provides power to the pump. A plurality of nozzles receive the pressurized insect control compound and generate an insect control compound mist. A controller receives a first command to cause the pump to begin operation and a wireless signal to cause the pump to stop operation.

Applicant believes that another reference corresponds to U.S. Patent Application Publication No. 20080067263 A1, published on Mar. 20, 2008 to Kemper O'neal Modlin, et al. for Automated Pest Misting System with Pump. However, it differs from the present invention because Modlin, et al. teaches a system and method for controlling adult populations of flying pests. A self-contained reservoir system for automated misting of pesticides is disclosed, which can be operated in remote location without the availability of line power or pressurized water. The automated spraying system comprises a secure controller unit with locking features, and a plurality of dispersing elements attached to the unit. Enclosed within the weatherproof and secure enclosure of the unit is a controller, pump, pesticide reservoir and power source for delivering controlled amounts of a pesticide mixture to the dispersing elements. The pump is capable of producing pressures sufficient for producing a mist from the dispersing elements. The pesticide reservoir holds pre-measured and premixed pesticide that can be used for direct treatment of an area. A misting schedule is entered into the controller, or timer. At the predetermined misting times, the controller completes the circuit between the battery and pump, thereby energizing the pump and causing the pesticide mixture to be pumped into the dispersing elements. The unit may be fitted with safety and efficiency components that automatically discontinue the misting cycles if someone is present in the area, weather conditions are not optimal, a fault is detected or pest activity is not favorable for a treatment.

Applicant believes that another reference corresponds to U.S. Patent Application Publication No. 20080029614 A1, published on Feb. 7, 2008 to David James Dore for Mist-Spraying Apparatus. However, it differs from the present invention because Dore teaches a mist-spraying apparatus primarily but not exclusively for use in an enclosed space that includes an air-blowing mechanism, a spraying mechanism and a control mechanism. The air-blowing mechanism defines an outlet conduit through which air can be blown and an inlet conduit through which air from within the space can be drawn. The spraying mechanism includes a pump for delivering liquid from a reservoir to an atomizing nozzle for spraying. The atomizing nozzle is located within the outlet conduit so that atomized particles emitted by the atomizing nozzle are entrained in the airstream emitted by the air-blowing mechanism and thereby distributed evenly throughout the space. The control mechanism controls operation and is adapted to commence operation of the air-blowing prior to operation of the atomizing nozzle and to continue operation of the air-blowing after operation of the nozzle has ceased.

Applicant believes that another reference corresponds to U.S. Pat. No. 9,414,580 B2 issued to Barry Franks, et al. on Aug. 16, 2016 for Heatless and Cordless Fogging/Misting Apparatus Having a Low CFM DC-Powered Blower Motor and a Mixing Chamber for Ultra-Low Volume Atomized Fog. However, it differs from the present invention because Franks, et al. teach a portable fogger apparatus that includes a portable fogger body having at least one airflow passageway. A DC blower motor is connected to the fogger body proximate to the airflow passageway and receives power from a battery, wherein the DC blower motor produces an airflow through the passageway. A mixing chamber is positioned along the at least one passageway, wherein at least a portion of the airflow is movable through the mixing chamber. A quantity of pressurized fogging liquid is housed within a container connected to the logger body. The pressurized fogging liquid is dispensable from the container into the mixing chamber where it is expelled through a nozzle and mixed with the airflow to produce a fog. The fog has an atomized micron particulate size between 5 and 60 microns. An activation controls activation of the DC blower motor and/or dispensing of the pressurized fogging liquid.

Applicant believes that another reference corresponds to U.S. Pat. No. 9,358,569 B2 issued to Diane Joyce Burt, et al. on Jun. 7, 2016 for Ultrasonic Surface Treatment Device and Method. However, it differs from the present invention because Burt, et al. teach devices, which generate a mist of a treatment composition, viz, an aerosolized treatment composition, which imparts a technical benefit to surfaces, or airspaces, which come into contact with the said aerosolized treatment composition. Also disclosed are methods for the treatment of surfaces.

Applicant believes that another reference corresponds to U.S. Pat. No. 8,994,529 B2 issued to Jeffrey C. White on Mar. 31, 2015 for Mosquito Misting System and Method for Using Same. However, it differs from the present invention because White teaches an apparatus and method for controlling and monitoring a mosquito misting system. The apparatus includes a chemical reservoir, a delivery system, a spray system, one or more sensors, a communication network and a misting management unit. The sensors may detect normal and abnormal operations of the misting system and send this data to the misting management unit. The misting management unit may then analyze the data and determine the problem. If the problem can be fixed without personnel, the misting management unit may simply adjust the system and fix the problem. If the problem requires personnel, the system may automatically schedule the service call based on a number of criteria.

Applicant believes that another reference corresponds to U.S. Pat. No. 8,430,337 B2 issued to Robert Clarence Pearce, III, et al. on Apr. 30, 2013 for Light-Activated Portable Aerosol Mist Sprayer Device. However, it differs from the present invention because Pearce, III, et al. teach a portable, light-activated, mist sprayer system comprising direct current power supply, an ambient light sensor, electronic circuitry that evaluates an electrical signal received from the light sensor to determine whether a "dusk" or "dawn" light condition exists; a container of treating fluid at a desired concentration; a motor and pump that are activated at the appropriate time as determined by the sensed light condition; at least one sprayer nozzle that will dispense a mist containing the treating fluid whenever the pump is operating; and a timer that turns off the pump after a preset interval to terminate the spraying cycle. A preferred utility for the system is spraying dilute solutions of insecticide or insect repellent during the periods of significant insect activity that typically occur around dusk and dawn. An RF receiving unit is also disclosed for optional activation using a remote transmitter.

Applicant believes that another reference corresponds to U.S. Pat. No. 7,540,433 B2 issued to John Fleming, et al. on Jun. 2, 2009 for Insect Control System and Method. However, it differs from the present invention because Fleming, et al. teaches an automated insect control system, which utilizes a container tank, a canned pump, distribution system, and a programmable digital timer to allow a user to control the times per day and the duration in which to apply insecticide to an area. A remote control is provided which permits a user to commence and terminate spraying of insecticide as the need arises without resorting to reprogramming of the spraying schedule.

Applicant believes that another reference corresponds to U.S. Pat. No. 7,320,439 B2 issued to Michael Davis, et al. on Jan. 22, 2008 for Self-Contained Insect Repelling and Killing Apparatus. However, it differs from the present invention because Davis, et al. teach an apparatus for the purpose of dispensing a chemical agent whose function is to detract or alternatively attract and destroy, insects, in particular, flying insects. The apparatus consists of a chemical source, a connection to a fluid source, usually water, a reservoir for chemical mixing and a pump for mixing and creating pressure. Mixing reservoir is of such size to eliminate any chance of chemical mixture separation and where the chemical mixture is agitated prior to each dispensing cycle. Fluid is disbursed under pressure through a series of atomizing devices, interconnected to the apparatus through a flexible plastic delivery conduit. The Apparatus functions are controlled through the use of an electronic interface. Preferred agent used is pyrethrum based, naturally occurring or synthesized, which possesses an antagonistic effect toward targeted pests but apparatus is designed to be adaptable to a wide-range chemicals.

Applicant believes that another reference corresponds to U.S. Pat. No. 7,090,147 B2 issued to Rod Lovett on Aug. 15, 2006 for Mosquito Misting System. However, it differs from the present invention because Lovett teaches a mosquito misting system having a liquid reservoir that is operably associated with a fluid pump and motor and fluid conduits to transmit a fluid insecticide to one or more dispersal nozzles. A controller is used to control the frequency and duration of dispersal. An agitator device is preferably associated with the fluid reservoir to adequately agitate the insecticide mixture within the reservoir during or just prior to dispersal of the fluid insecticide. The controller is interconnected with a level sensor assembly to provide a graphic indication of the level of fluid insecticide remaining in the reservoir. Additionally, the misting system is provided with a fluid pressure switch that detects a rupture in the fluid conduit and prevents further flow of fluid from the reservoir. In further aspects, the system is provided with remote control and, optionally, a remote monitoring feature that allows improved service and maintenance for the system.

Other patents describing the closest subject matter provide for a number of more or less complicated features that fail to solve the problem in an efficient and economical way. None of these patents suggest the novel features of the present invention.

SUMMARY OF THE INVENTION

The present invention is a misting system, comprising an external compartment, an interior housing, a container housing, an electrical compartment, a lid assembly and at least one outlet.

The external compartment comprises a top face with a hole, an internal lateral face, an external lateral face, a first bottom face, an interior face to define a cavity, and an electrical cover panel. The internal lateral face comprises first and second exterior rails for an upper bridge plate and a lower bridge plate respectively.

The interior housing comprises a top face with a hole, first and second lateral faces, a bottom face and interior faces. The lateral faces each comprise a pivot hole and at least one lateral protrusion.

The container housing comprises an access panel, lateral faces, interior faces and a bottom face. The lateral faces each comprise a pivoting protrusion, which are positioned onto each pivot hole of the interior housing lateral faces.

The electrical compartment comprises an upper external face, an external lateral face, an internal lateral face, a bottom face, and a cover panel. The electrical compartment further comprises a battery, a pump assembly, a switch, an external charge receptor, a connector and a controller. The internal lateral face comprises a pump mount hole to secure the pump assembly. The lid assembly comprises a lid, a locking tab, a panel locking tab, a latching-limiter rod, and a spear.

A chemical container is used in the present invention. It comprises a cap, and a foil. The chemical container is positioned in the container housing, the container housing is positioned in the interior housing, and the interior housing is positioned in the cavity of the external compartment. The electrical cover panel of the external compartment mounts onto the electrical compartment, and the cover panel of the electrical compartment mounts onto the external compartment. The lid assembly covers the external compartment and the electrical compartment.

It is therefore one of the main objects of the present invention to provide a misting system.

It is another object of this invention to provide a misting system, wherein a chemical container contains premixed chemical compositions to kill insects such as mosquitos when sprayed or dispensed.

It is another object of this invention to provide a misting system that does not require trained installers.

It is another object of this invention to provide a misting system that stores energy for protection when power is out or unavailable for a long period of time.

It is another object of this invention to provide a misting system that recharges via solar, AC, or 12 vdc source.

It is another object of this invention to provide a misting system, whereby a supplied battery charger works with 110-240 vac at 50-60 cycles.

It is another object of this invention to provide a misting system that comprises a remote, wireless control and on-off switch, which can both be used to energize the self-priming pump. The self-priming pump can run dry without damage.

It is another object of this invention to provide a misting system that is portable and suitable for campers, boats, barns, recreational vehicles, etc.

It is another object of this invention to provide a misting system that is an affordable, lightweight, do-it-yourself solution.

It is another object of this invention to provide a misting system that puts premixed chemical compositions on insects and pests.

It is another object of this invention to provide a misting system that dispenses premixed chemical compositions through an outlet such as at least one nozzle, or to drift onto or be blower assisted to contact insects and pests.

It is another object of this invention to provide a misting system that can be used for, but not limited to, mosquito and pest control, killing insects and pests, and the application of fungicide, surfactants, insecticides, scents, herbicide, enzymes solutions, fertilizers, biocides, oxidizers, and/or any combinations thereof.

It is another object of this invention to provide a misting system with at least one outlet such as nozzles that can be cooperatively arranged on an oscillating fan to increase spray range and throw.

It is another object of this invention to provide a misting system having a secured container housing that prevents physical contact with premixed chemical compositions.

It is another object of this invention to provide a misting system that is volumetrically efficient for carrying, transporting, and storage.

It is another object of this invention to provide a misting system that can be readily assembled and disassembled without the need of any special tools.

It is another object of this invention to provide a misting system, which is of a durable and reliable construction.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 1:
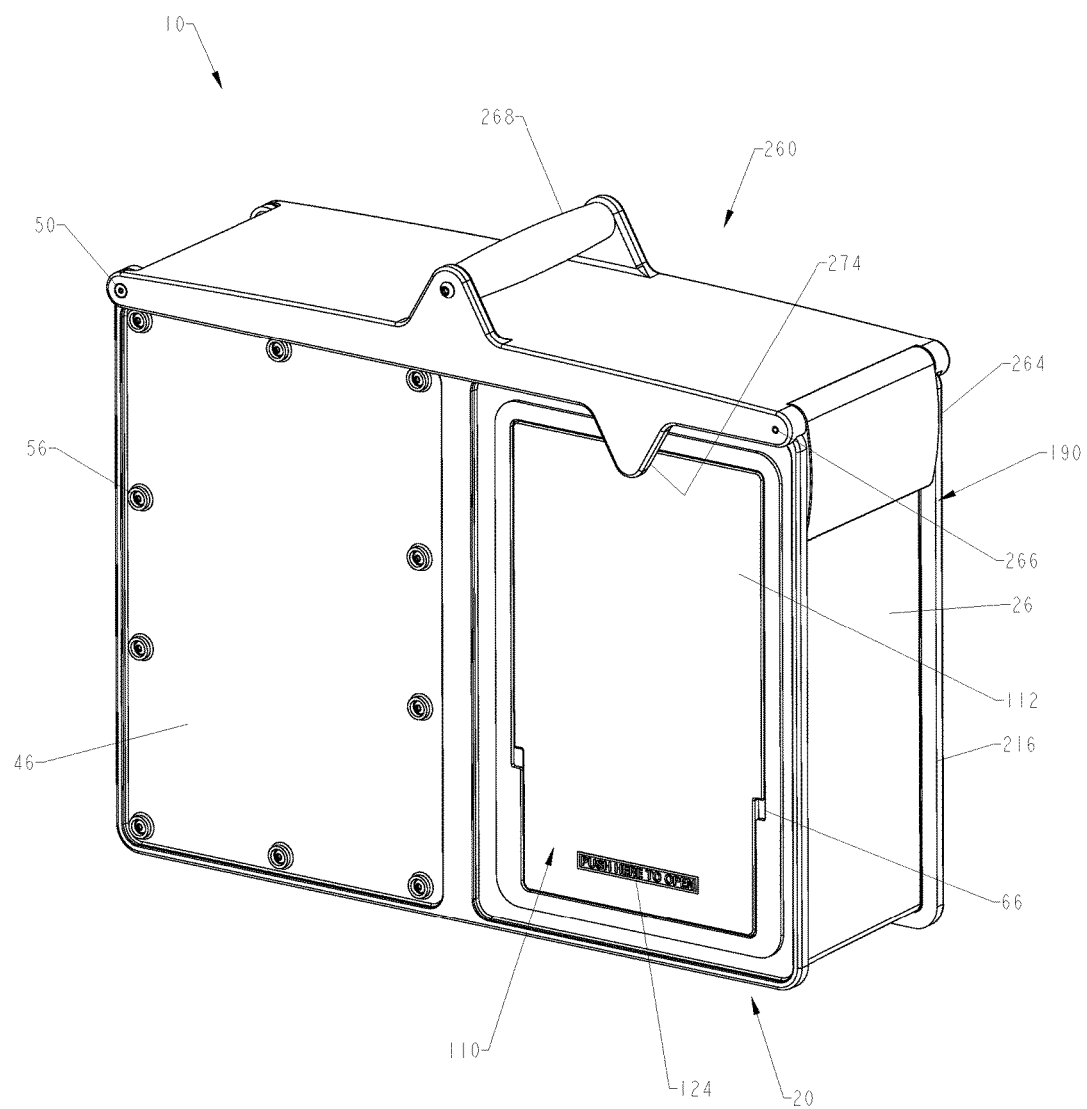
FIG. 1 is a first isometric view of the present invention.

Referring now to the drawings, the present invention is a misting system and is generally referred to with numeral 10. It can be observed that it basically includes external compartment 20, interior housing 70, container housing 110, at least one outlet 252, electrical compartment 190, and lid assembly 260.

Figure 2:
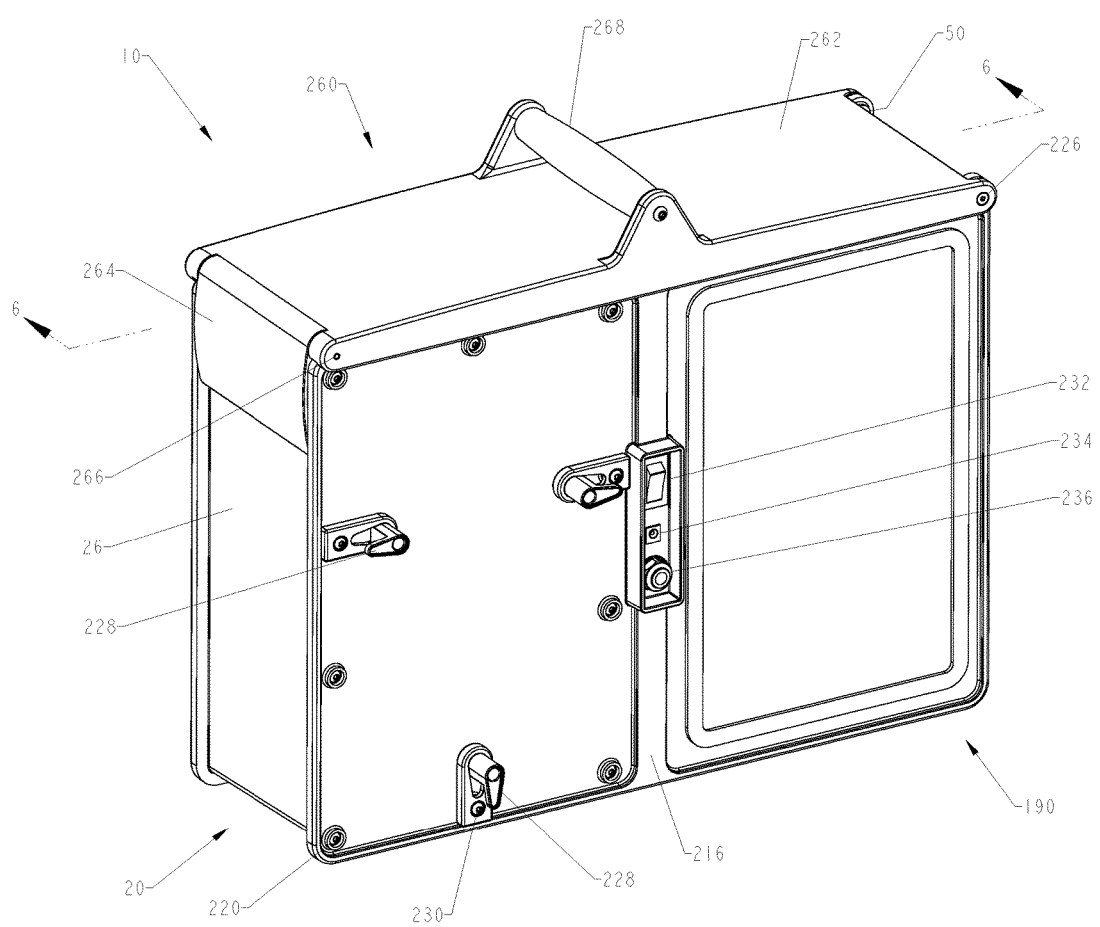
FIG. 2 is a second isometric view of the present invention.

As seen in FIGS. 1 and 2, misting system 10 comprises external compartment 20, which houses container housing 110.

External compartment 20 comprises electrical cover panel 46 that mounts onto electrical compartment 190 with screws 56, and cover panel 216 of electrical compartment 190 that mounts onto external compartment 20 with screws 220.

Lid assembly 260 covers external compartment 20 and electrical compartment 190, and latches onto external lateral face 26 with locking tab 264. When lid assembly 260 is in a closed configuration, panel locking tab 274 blocks access panel 112 and prevents it from opening. It is noted that external compartment 20 is a "wet compartment" comprising chemical container 140, seen in FIG. 3. It is noted that electrical compartment 190 is a "dry compartment" comprising electrical components as defined below and is an opposite side of external compartment 20.

Switch 232, external battery charger receptor 234, connector 236, and hooks 228, secured by screws 230, are positioned on cover panel 216 of electrical compartment 190. Switch 232 is an "on/off" switch to able and disable present invention 10. Hooks 228 are used to store exterior tubing 300 in shipping and in portable travel. External battery charger receptor 234 is a receptacle for charging from a fast/float charger, solar charger or an external 12V source like a car or boat battery or cigarette lighter plug. Connector 236 is utilized to secure exterior tubing for chemical composition 304 to travel through, seen in FIG. 9. Chemical composition 304 is therefore a premixed, self contained chemical.

Figure 3:
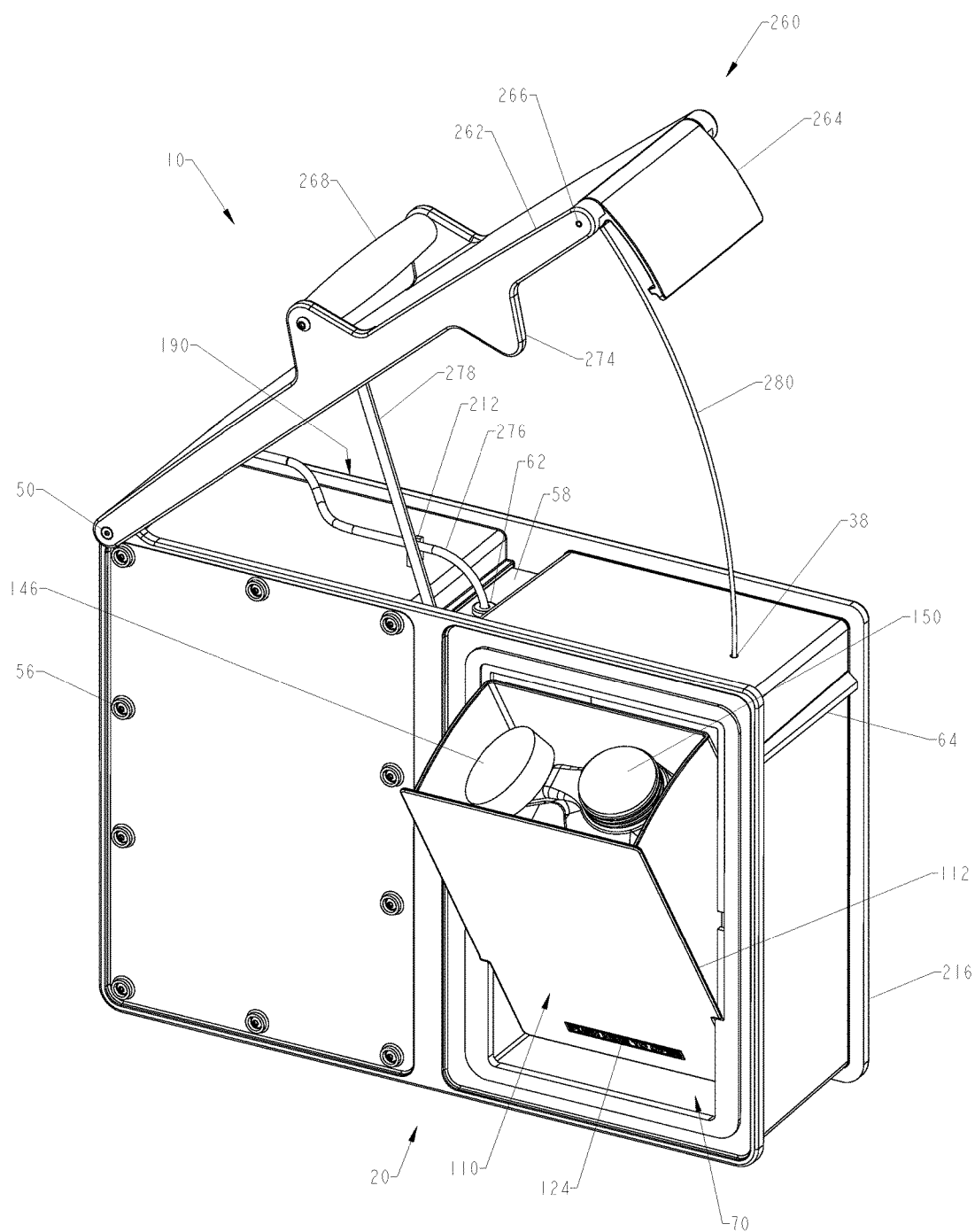
FIG. 3 is a third isometric view of the present invention with its container housing and lid assembly opened.
Figure 4:
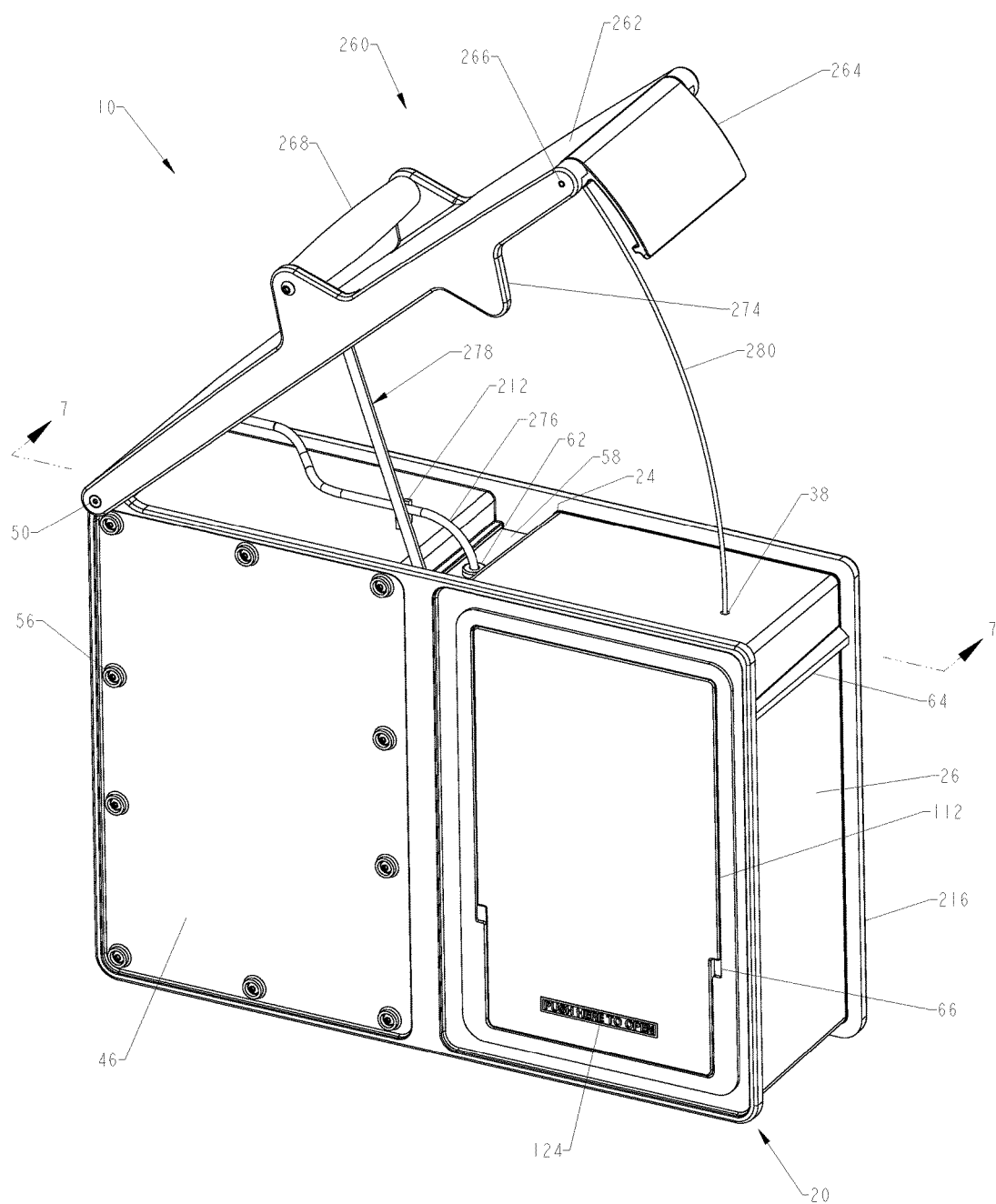
FIG. 4 is a fourth isometric view of the present invention with its container housing closed and lid assembly opened.

As seen in FIGS. 3 and 4, lid assembly 260 comprises spear 280, which enters into external compartment 20 at hole 38. Upper bridge plate 58 has grommet 62 that receives tubing 276 therethrough and into present invention 10. When lid assembly 260 is in an opened configuration, panel locking tab 274 does not block access panel 112. Thereby, allowing access panel 112 to open, wherein container housing 110 pivots upon pivoting protrusions 122 positioned with respective pivot holes 90 of interior housing 70, seen in FIG. 5. Container housing 110 houses chemical container 140. Chemical container 140 comprises premixed chemical composition 304, seen in FIG. 9, and the shipped chemical container 140 itself is a temporary container until it expires. Chemical container 140 requires no mixing of chemical composition 304, seen in FIG. 9, and there is no chemical exposure from chemical mixing.

It is noted that chemical container 140 arrives with cap 146 on, covering foil 150 below. However, cap 146 must first be removed and can be stored inside container housing 110 since spear 280 is not designed to pierce cap 146, instead it is designed to pierce foil 150. In a preferred embodiment, container housing 110 tolerances prevent it from being closed while cap 146 is still on chemical container 140. Therefore, once cap 146 has been removed, container housing 110 is first closed, and then lid assembly 260 is closed, causing spear 280 to pass through hole 92 and pierce foil 150 and travel to a lower biased corner of chemical container 140 as a chemical pickup.

Figure 5:
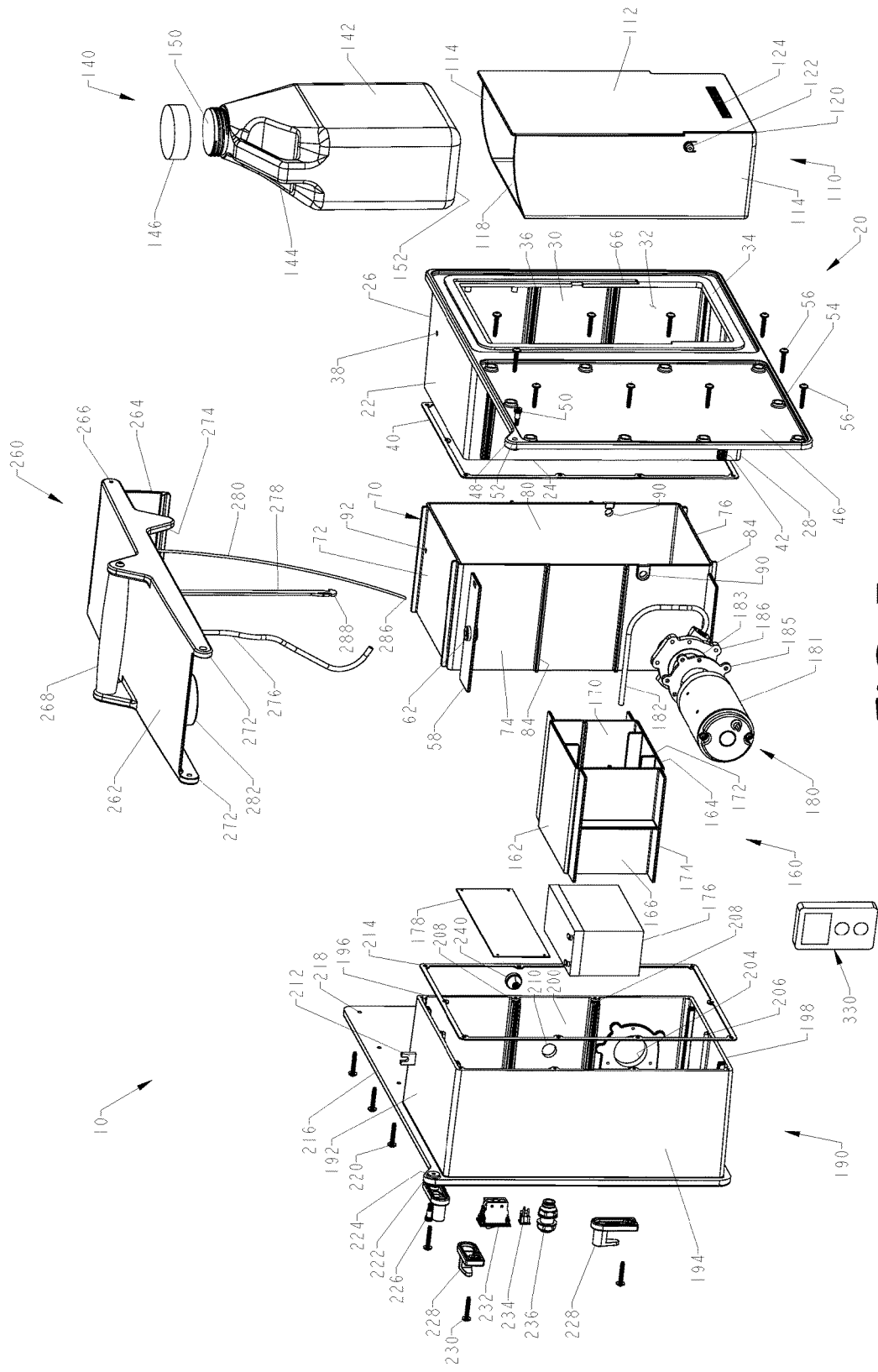
FIG. 5 is an exploded view of the present invention.

As seen in FIG. 5, external compartment 20 comprises top face 22, internal lateral face 24, external lateral face 26, bottom face 28, frame 34 with stop lip 66, gasket 40, and interior faces 30 to define cavity 32. External compartment 20 further comprises electrical cover panel 46, which has tab 48 with hole 52 to receive pin 50. Electrical cover panel 46 further comprises screw holes 54 to receive screws 56.

Interior housing 70 comprises top face 72 with hole 92, lateral faces 74, bottom face 76, and interior faces 80. Lateral faces 74 each comprises pivot hole 90.

Container housing 110 comprises access panel 112, lateral faces 114, interior faces 118, bottom face 120 and instruction placard 124. Instruction placard 124 may for example read "Push here to open". Lateral faces 114 each comprises pivoting protrusion 122, which fit into a respective pivot hole 90.

Battery housing 160 comprises top face 162, bottom face 164, exterior lateral faces 166, and interior faces 170 with positioning walls 172. Battery housing 160 houses battery 176. In a preferred embodiment, battery 176 is a rechargeable battery that charges from its fast/float switching charger able to accept any AC power source 110-240 VAC, 50-60 Hz, or solar charger or except a charge from a 12 VDC source like a car or boat cigarette lighter or battery connection.

Electrical compartment 190 comprises upper external face 192 with tubing support ribs 212, external lateral face 194, internal lateral face 196 with pump mount hole 204 and access hole 210, bottom face 198, interior lateral faces 200, cover panel 216, and water-tight grommet 240.

Pump mount hole 204 is built up thick to strengthen and acts as a much needed spacer with this style of pump assembly 180.

Electrical compartment 190 further comprises panel mount holes 206. Electrical cover panel 46 covers gasket 214 to mount onto electrical compartment 190. Cover panel 216 comprises tab 222 with hole 224 to receive pin 226. Screws 220 extend through holes 218 to mount cover panel 216 onto external compartment 20 as seen in FIG. 2.

Lid assembly 260 comprises lid 262 having locking tab 264 secured by pin 266. Lid assembly 260 further comprises pivot holes 272, which allow lid assembly 260 to be secured to tab 48 of electrical cover panel 46 with pin 50, and tab 222 of cover panel 216 with pin 226, as seen assembled in FIGS. 2 and 4. Lid assembly 260 further comprises hinge and handle 268, tubing 276, latching-limiter rod 278 with rod end 288, and spear 280 with spear tip 286.

Chemical container 140 comprises sidewalls 142, handle 144, cap 146, and foil 150. It is noted that cap 146 can be stored in container housing 110, and foil 150 is unpierced in this illustration. Chemical container 140, houses chemical composition 304 seen in FIG. 9.

In one embodiment, present invention 10 is a portable RF remote controllable apparatus, whereby a receiver antenna is internal to the electrical compartment 190 and not exposed. Such a remote controllable apparatus can be for example wireless remote 330.

Figure 6:
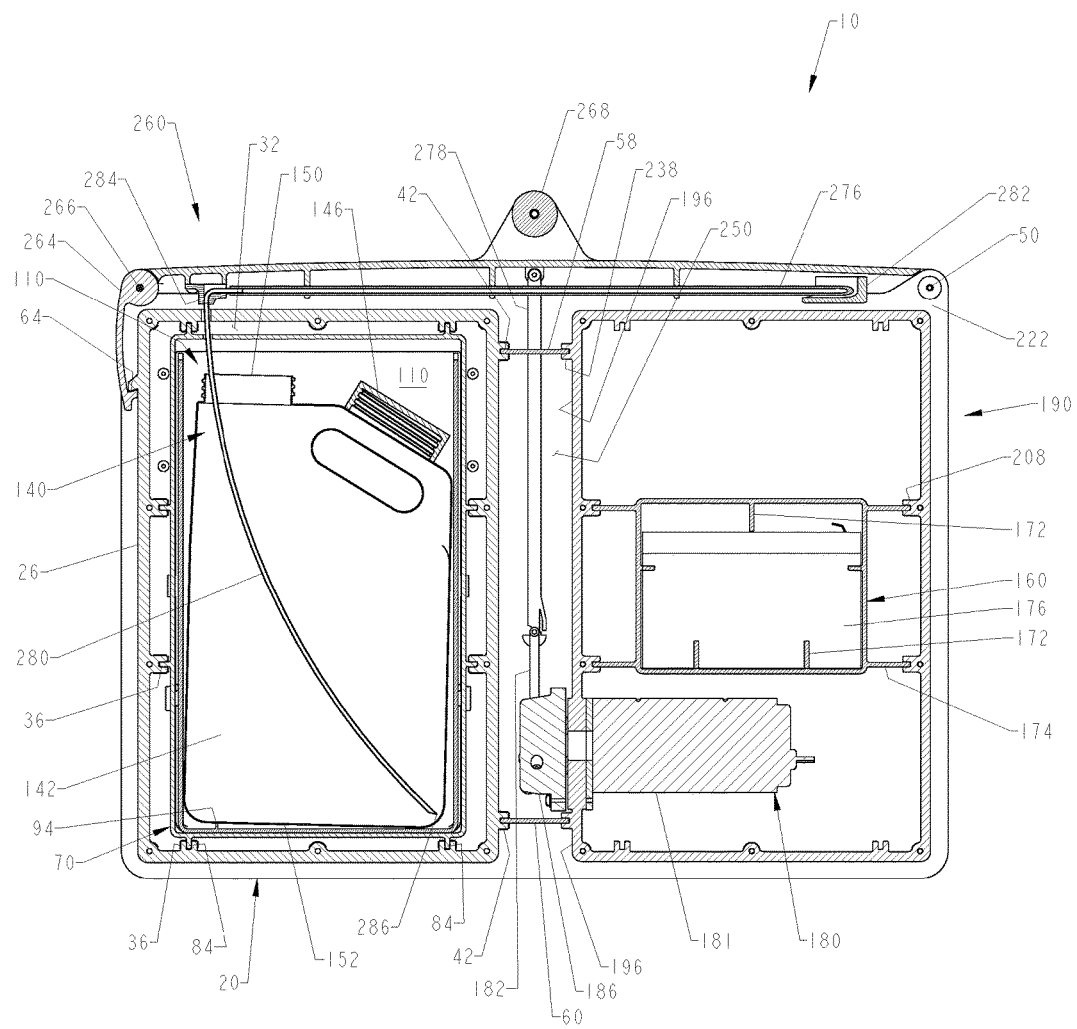
FIG. 6 is a cut view taken along the lines 6-6 as seen in FIG. 2.

Seen in FIG. 6 is internal cavity 250 that serves as a third compartment containing both electrical and wet elements like pump head assembly 186 and fluid tubes as well as power wires and switches as defined herein, whereby chemical container 140 is positioned in container housing 110, container housing 110 is positioned in interior housing 70, and interior housing 70 is positioned in cavity 32 of external compartment 20. Protrusions 84 of interior housing 70 are fixed to interior rails 36 of external compartment 20. Pump assembly 180 comprises pump motor 181, positioned in electric compartment 190, and pump head assembly 186, positioned in internal cavity 250. This allows pump motor 181 to enjoy the dry compartment while pump head assembly 186 inhabits a non-dry environment. In an alternate embodiment, external compartment 20 can be larger, whereby components within internal cavity 250 would be instead inside external compartment 20, thus eliminating internal cavity 250

Battery 176 is secured by battery housing 160 with positioning walls 172. Battery housing 160 is fixed to electrical compartment 190 by mounting tabs 174 on interior rails 208. Pump assembly 180 with output tubing 182 is positioned on pump mount hole 204, seen in FIG. 5, of internal lateral face 196.

Upper bridge plate 58 and lower bridge plate 60 are each fixed to exterior rails 42 of external compartment 20 and exterior rails 238 of electrical compartment 190. Latching-limiter rod 278 passes through hole 68 of upper bridge plate 58 as seen in FIG. 5.

Spear base 284 secures spear 280 on lid assembly 260. In addition, tube retainer 282 secures tubing 276. As lid assembly 260 is being closed, spear 280, guided by hole 38 of external compartment 20, passes through hole 92 of internal housing 70, then pierces foil 150 to be positioned inside chemical container 140. Lid assembly 260 closes when locking tab 264 engages onto clasp 64 positioned on external lateral face 26 of external compartment 20. In a preferred embodiment, spear 280 has sufficient curvature or radial arc to enter chemical container 140 through foil 150 and extend approximately diagonally towards, but without reaching, container base 152. It is noted that spear tip 286 will not contact container base 152. Present invention 10 operates when lid assembly 260 is in the closed configuration and switch 232 is in "on" position. Wedge 94 is located at one corner of bottom face 120 to tilt chemical container 140. More specifically, wedge 94 inside bottom of container housing 110 tips chemical container 140 towards spear 280 to allow chemical composition 304 to be biased in favor of being picked up by spear 280 when chemical container 140 is near empty. Cap 146 may optionally be placed within container housing 110.

Figure 8:
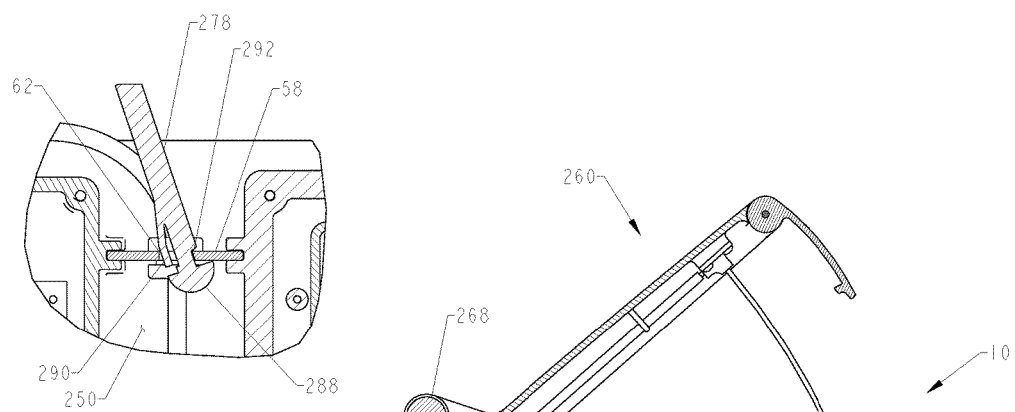
FIG. 8 is a close up view as seen in FIG. 7.
Figure 7:
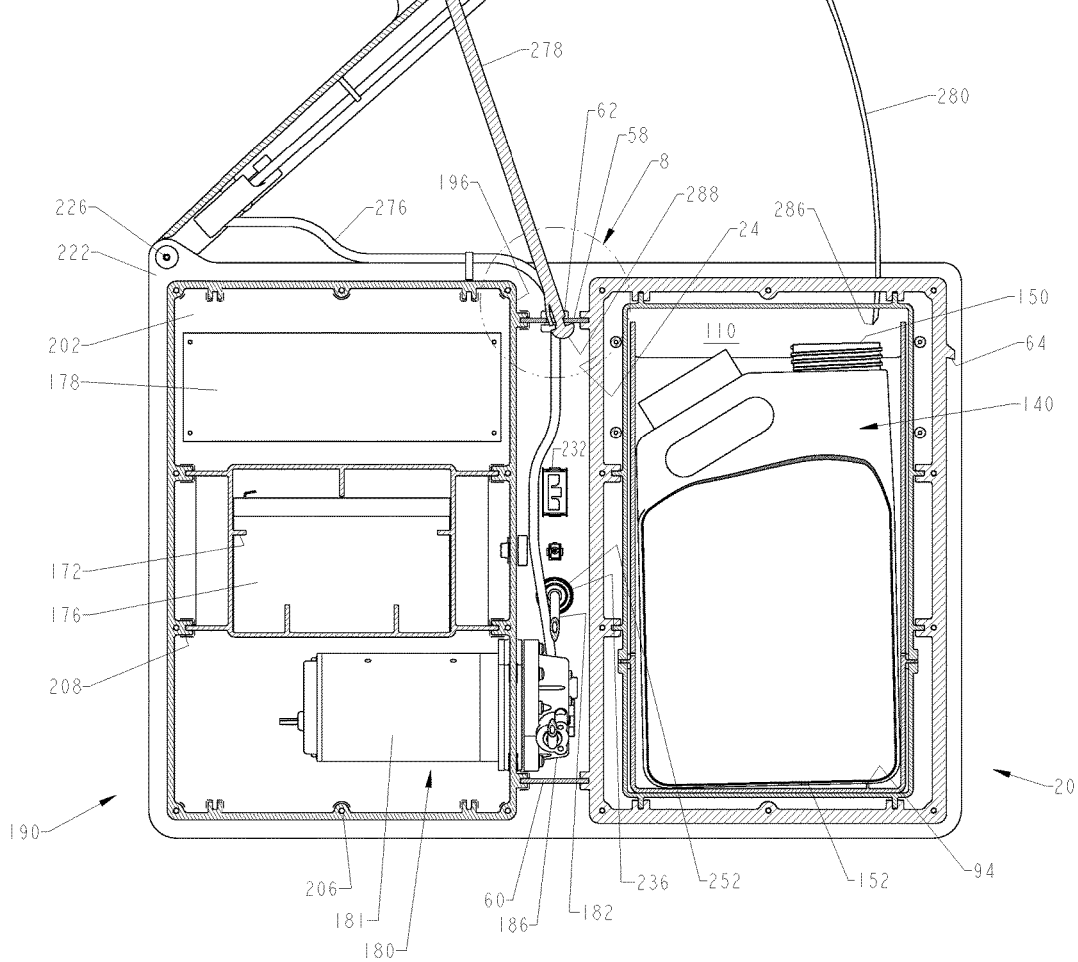
FIG. 7 is a cut view taken along the lines 7-7 as seen in FIG. 4.

As seen in FIGS. 7 and 8, electrical compartment 190 houses pump assembly 180, battery 176, controller 178 with an RF receiver, watertight connections from pump assembly 180 to pump motor 181 and from external battery charger receptor 234 to battery 176 by way of access hole 210 utilizing water-tight grommet 240.

Tubing 276 extends from spear 280 and passes through grommet 62 to connect to pump assembly 180. When operating present invention 10, chemical composition 304, seen in FIG. 9, flows through spear 280, through tubing 276, and is pumped through output tubing 182 to outlet 252 having connector 236 mounted thereon at cover panel 216, seen in FIG. 2. Connector 236 is a fitting to connect exterior tubing/line from present invention 10. Controller 178 is positioned on interior back face 202 of electrical compartment 190. Rod end 288 is a stopper to prevent spear tip 286 from exiting external compartment 20 when lid assembly 260 is opened. Detent 292 props lid assembly 260 up to safely swap out chemical container 140, whereby cantilever 290 acts like a spring and pushes latching-limiter rod 278 aside when lid assembly 260 is opened a predetermined distance. Detent 292 engages upper bridge plate 58 to temporarily lock lid assembly 260 in the up position. By placing a predetermined force onto latching-limiter rod 278 (leftward direction in FIGS. 7 and 8), cantilever 290 will deflect. Thus, releasing detent 292 from resting on upper bridge plate 58, and lid assembly 260 closes. More specifically, latching-limiter rod 278 will stop lid assembly 260 from over rotation, whereby detent 292 stays engaged upper bridge plate 58. An angle of uppermost detent 292 is designed to release upon lid assembly 260 being pushed down, which in turn pushes down on latching-limiter rod 278, causing detent 292 to return to a down position by glancing off upper bridge plate 58 due to an angle of face.

Figure 9:
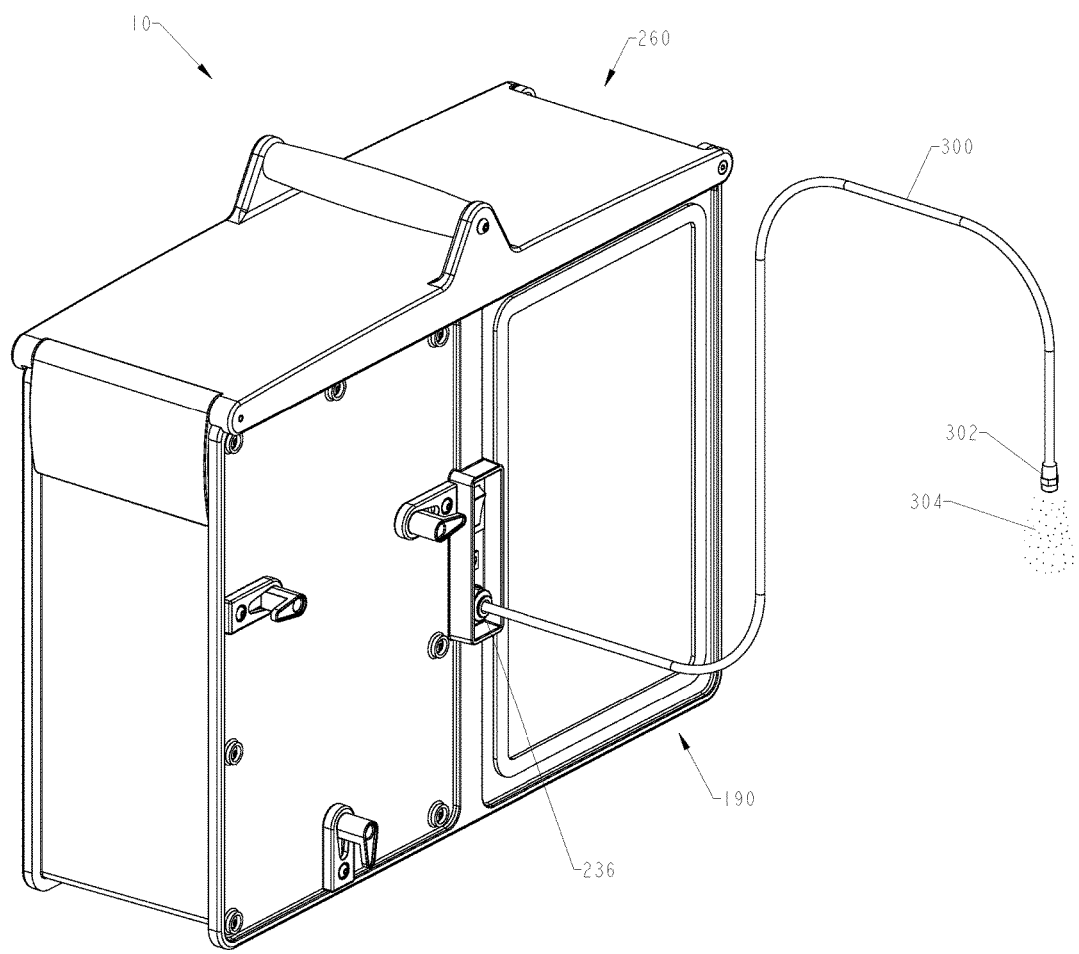
FIG. 9 is a fifth isometric view of the present invention spraying a chemical composition.

As seen in FIG. 9, exterior tubing 300 may attach to connector 236. Exterior tubing 300 may comprise at least one nozzle 302 to emit chemical composition 304 in a mist, sprayed, and/or stream manner. In a preferred embodiment, chemical composition 304 is a premixed insecticide to repel and/or kill insects and particularly mosquitos, no-see-ums, and black fly.

Figure 10:
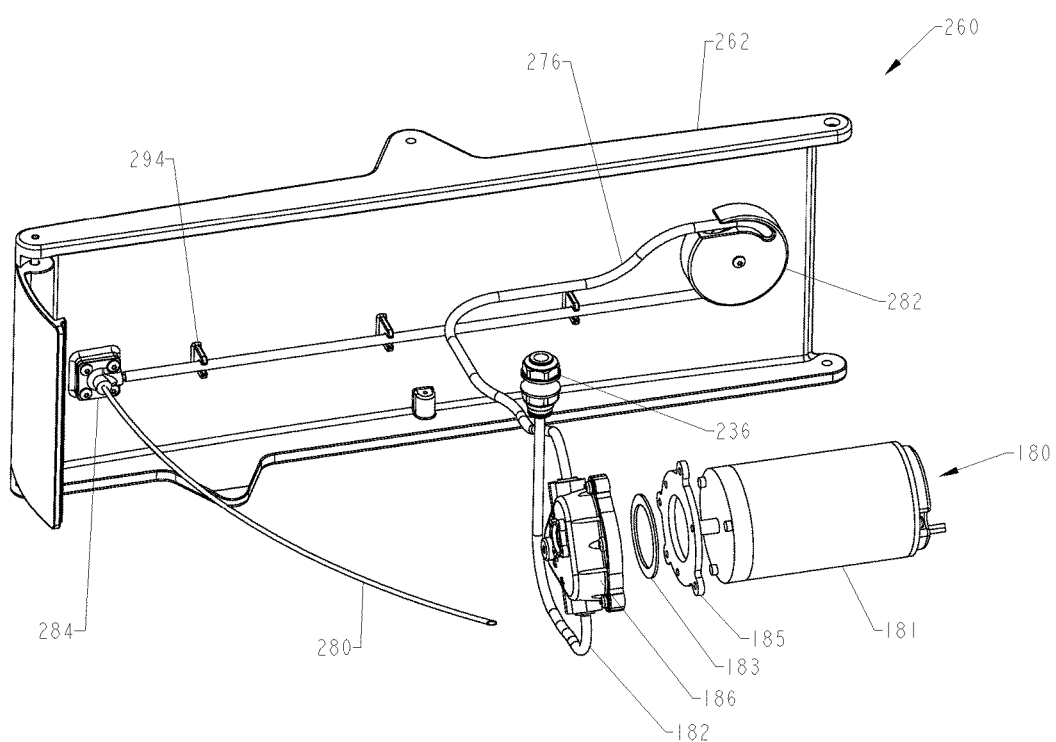
FIG. 10 is a bottom view of the lid assembly and tubing connecting to and from a pump assembly.

As seen in FIG. 10, spear base 284 secures spear 280 on lid assembly 260. Tube clamps 294 and tube retainer 282 secures tubing 276 at all operating angles. Tubing 276 connects to pump assembly 180. Pump assembly 180 comprises pump motor 181, pump seal 183, spacer 185, pump head assembly 186. When operating present invention 10, chemical composition 304, seen in FIG. 9, flows through spear 280, through tubing 276, and is pumped through output tubing 182 to outlet 252 having connector 236.

Present invention 10 dispenses chemical composition 304 of chemical container 140 through remote misting nozzles to drift onto or be blower assisted to contact its subjects. Present invention 10 provides a plurality of functions depending on chemical composition 304 utilized. Although primarily intended for mosquito pest control, killing insects and pests; present invention 10 also can be used for the application of fungicide, surfactants, insecticides, scents, herbicide, enzyme solutions, fertilizers, biocides, oxidizers, and/or any combinations thereof. In another embodiment, present invention 10 can control an oscillating fan remotely through a line carrier controlled relay allowing present invention 10 to turn on the fan, not seen, only while spraying to improve range. Present invention 10 is lightweight and portable suitable for campers, boats, and barns, and can run months on a single charge of battery 176. Present invention 10 may also comprise a charger.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A misting system, comprising:
    A) an external compartment, said external compartment houses a premixed, self contained chemical;
    B) an interior housing comprising a first top face with a hole, first and second laterals faces, a first bottom face, and first interior faces, said first and second lateral faces each comprise a pivot hole and at least one lateral protrusion;
    C) a container housing comprising an access panel, third and fourth lateral faces, second interior faces, and a second bottom face, said third and fourth lateral faces each comprise a pivoting protrusion which are positioned onto each said pivot hole;
    D) an electrical compartment;
    E) a lid assembly comprising a lid, a locking tab, and a panel locking tab, said lid assembly covers said external compartment and said electrical compartment, whereby said panel locking tab blocks access to said access panel and prevents it from opening at a closed configuration; and
    F) at least one outlet configured to spray the premixed, self contained chemical.

2. The misting system set forth in claim 1, further characterized in that said external compartment comprises a second top face, a first internal lateral face, a first external lateral face, a third bottom face, an interior face to define a cavity, and an electrical cover panel.

3. The misting system set forth in claim 2, further characterized in that said second top face comprises a hole.

4. The misting system set forth in claim 2, further characterized in that said first internal lateral face comprises a first and a second exterior rails.

5. The misting system set forth in claim 4, further characterized in that said external compartment comprises an upper bridge plate and a lower bridge plate that are each connected to said respective first and second exterior rails.

6. The misting system set forth in claim 1, further characterized in that a chemical container is placed inside said container housing.

7. The misting system set forth in claim 6, further characterized in that said chemical container comprises a cap, and a foil.

8. The misting system set forth in claim 2, further characterized in that said electrical compartment comprises an upper external face, a second external lateral face, a second internal lateral face, a fourth bottom face, and a cover panel.

9. The misting system set forth in claim 8, further characterized in that said electrical compartment comprises a battery, a pump assembly, and a controller.

10. The misting system set forth in claim 9, further characterized in that said second internal lateral face comprises a pump mount hole to secure said pump assembly.

11. The misting system set forth in claim 1, further characterized in that said electrical compartment comprises a switch, an external charge receptor, and a connector.

12. The misting system set forth in claim 1, further characterized in that said lid assembly comprises a latching-limiter rod, and a spear.

13. The misting system set forth in claim 2, further characterized in that a chemical container is positioned in said container housing, said container housing is positioned in said interior housing, said interior housing is positioned in said cavity of said external compartment.

14. The misting system set forth in claim 8, further characterized in that said electrical cover panel of said external compartment mounts onto said electrical compartment, and said cover panel of said electrical compartment mounts onto said external compartment.

15. The misting system set forth in claim 1, further characterized in that said lid assembly covers said external compartment and said electrical compartment.

* * * * *